United States Patent [19]

Bardos et al.

[11] Patent Number: 4,782,142
[45] Date of Patent: Nov. 1, 1988

[54] NOVEL 5-SUBSTITUTED 2-PYRIMIDINONE NUCLEOSIDES AND METHODS OF USE

[75] Inventors: Thomas J. Bardos, Snyder, N.Y.; Yung-Chi Cheng, Chapel Hill, N.C.; Alan C. Schroeder, Silver Spring, Md.; Simon M. N. Efange, Buffalo, N.Y.

[73] Assignee: The Research Foundation of State University of New York, Albany, N.Y.

[21] Appl. No.: 641,770

[22] Filed: Aug. 20, 1984

Related U.S. Application Data

[63] Continuation-in-part of Ser. No. 337,297, Jan. 5, 1982, Pat. No. 4,468,384.

[51] Int. Cl.$^4$ .................... C07H 19/04; C07H 19/073
[52] U.S. Cl. ........................................ 536/23; 536/29
[58] Field of Search ........................... 536/23, 29

[56] References Cited

U.S. PATENT DOCUMENTS

| | | | |
|---|---|---|---|
| 4,382,925 | 5/1983 | de Clercq et al. | 536/23 |
| 4,386,076 | 5/1983 | Machida et al. | 536/23 |
| 4,395,406 | 7/1983 | Gacek et al. | 424/180 |

OTHER PUBLICATIONS

Chemical Abstracts, vol. 93, Abst. No. 186752v, 1980.
Chemical Abstracts, vol. 93, Abst. No. 88454e, 1980.
In re Grabiak, 226 USPQ 870 (1985) pp. 870–873.
Oyen et al, "5–Fluoropyrimidin–2–one Deoxyriboside and Its Growth Inhibiting Properties", *Biochim. Biophys. Acta*, 182 (1969) pp. 567–569.
Votruba, I. et al, "Mechanism of Inhibition of DNA Synthesis in Escherichia Coli by Pyrimidin–2–one β–D–Ribofuranoside", *Biochimica et Biophysica Acta*, 324 (1973) pp. 14–23.
Laland, S. G. et al, "Synthesis of Pyrimidin–2–one Deoxyribosides and Their Ability to Support the Growth of the Deoxyriboside-Requiring Organism Lactobacillus acidophilus R26", *Biochem. Journal*, 90 (1964) pp. 76–81.
Oyen, T. B., "Synthesis and Properties of Ribosyl-pyrimidin–2–One", *Biochimica et Biophysica Acta*, 186 (1969) pp. 237–243.
Oftebro, R. et al, "5–Fluoropyrimidin–2–one, A New Metaphase Arresting Agent", *Biochemical Pharmacology*, 21 (1972) pp. 2451–2456.
McCormack, et al, "Inhibition of Cytidine Deaminase by 2–Oxopyrimidine Riboside and Related Compounds", *Biochemical Pharmacology*, 29 (1980) pp. 830–832.
Doskocil et al, "Inhibition of Nucleoside-binding Sites by Nucleoside Analogues in Escherichia coli", *Nucleic Acids Research*, (1974) pp. 491–502.
Cheng et al, "Properties of Herpesvirus-Specific Thymidine Kinase, DNA Polymerase and DNase and Their Implication in the Development of Specific Antiherpes Agents", *Advances in Ophthalmology*, 38 (1979) pp. 173–186.
Prusoff et al, "Role of Nucleosides in Virus and Cancer Chemotherapy", *Advances in Opthalmology*, 38 (1979) pp. 3–16.
Johns, D. G., "Human Liver Aldehyde Oxidase: Differential Inhibition of Oxidation of Charged and Uncharged Substrates", *Journal of Clinical Investigation*, 46 (1967) No. 9, pp. 1492–1505.
Helgeland et al, "The Synthesis, Characterization and Biological Properties of a New Substance, 5--Fluoropyrimidin-2-one", *Biochim. Biophys. Acta*, 87 (1964) pp. 353–355.
Oyen, T. B. et al, "Preparation and Biological Properties of Deoxyribosides and Deoxyribotides of Pyrimidin–2–one", *Biochem. Journal* 92 (1964) pp. 27P-28 P.
Renis, H. E., "Pyrimidines and Their Nucleosides", *Antibiotics Chemotherapy*, 27 (1980) pp. 164–207.
Wightman, R. et al, "Nucleic Acid Components and Their Analogues Clix. Synthesis of Some 2–Pyrimidone Nucleosides", *Collection of Czechoslov. Chemical Communications*, 38 (1973) pp. 1381–1397.

(List continued on next page.)

*Primary Examiner*—Blondel Hazel
*Attorney, Agent, or Firm*—Howard M. Ellis; Michael L. Dunn

[57] ABSTRACT

Compounds for inhibiting the replication of DNA viruses which induce the formation of thymidine kinase enzyme of the formula:

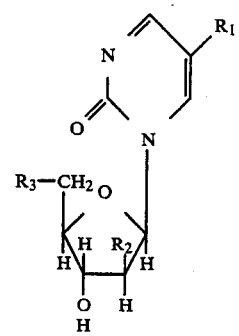

wherein $R_1$ is a radical selected from the group consisting of chloro, iodo, hydroxy, alkoxyalkyl, hydroxyalkyl, methylamino, formyl, nitro, and unsubstituted hydrocarbon groups of 2 to about 3 carbon atoms or halo-substituted hydrocarbon groups of 1 to about 3 carbon atoms; $R_2$ is hydrogen or hydroxy; and $R_3$ is hydroxy, $-OP(O)(OH)_2$, amino, or $-OCOR_4$ where $R_4$ is alkyl or alkoxyalkyl of 2 to about 18 carbon atoms.

3 Claims, No Drawings

OTHER PUBLICATIONS

Kohler, P. et al, "Anomeric (1-(2-Deoxy-D-Erythro-Pentofuranosyl-2(1H)-Pyrimidinones", *Nucleic Acid Chemistry*, John Wiley & Sons, N.Y. (1978) pp. 283-289.

Torrence, P. F. et al, "Synthesis and Antiviral Activities of New 5-Substituted Pyrimidine Nucleoside Analogs"; *Frontiers in Bioorganic Chemistry and Molecular Biology*, (1979) pp. 59-85.

Johns et al, "Enzymic Hydroxylation of 5-Fluoropyrimidines by Aldehyde Oxidase and Xanthine Oxidase", *Biochemical Pharmacology* 15 (1966) pp. 400-403.

Prusoff, W. H. et al, "Antiviral Iodinated Pyrimidine Deoxyribonucleosides: 5-IODO-2'-Deoxyuridine; 5 IODO-2'-Deoxycytidine; 5-IODO-5'-Amino-2',5'-Dideoxyuridine", *Pharmaceutical Therapy*, 7 (1979) pp. 1-34.

Nakayama, C. et al, "Synthetic Nucleosides and Nucleotides. XII. Synthesis and Antiviral Activities of Several 1-β-D-Arabinofuranosyl-5-Alkyluracils and Their Monophosphates", *Carbohydrates-Nucleosides-Nucleotides*, Marcel Dekker, Inc., 6(4), pp. 295-308.

Sakata, S. et al, "Synthesis and Antiherpesviral Activity of 5-C-Substituted Uracil Nucleosides", *Nucleic Acids Research*, 8 (1980) pp. 39-42.

NOVEL 5-SUBSTITUTED 2-PYRIMIDINONE NUCLEOSIDES AND METHODS OF USE

This invention was made with government support under a Public Health Service Research Grant from the National Cancer Institute: 5-ROI-CA-06695. The government has certain rights to this invention.

CROSS-REFERENCE TO RELATED APPLICATION

This is a continuation-in-part of application Ser. No. 337,297, filed Jan. 5, 1982, now U.S. Pat. No. 4,468,384.

BACKGROUND OF THE INVENTION

1. Field of the Invention

This invention relates to novel compounds and methods which are useful for inhibiting the replication of DNA viruses, and more particularly, relates to compounds for inhibiting the replication of DNA viruses which induce the formation of thymidine kinase enzyme.

2. History of the Prior Art

Historically, viruses have been the causative agents of many diseases of both plants and animals including man. Diseases caused by viruses have been very difficult to control or cure by traditional methods. Many such viral diseases have been, in the past, effectively controlled through mass vaccination but even in modern times, effective agents to cure viral diseases, rather than prevent them, have been unavailable.

It has been recently discovered that certain substituted naturally occurring pyrimidinones are effective antiviral agents. Most of such compounds are 5-substituted pyrimidinones attached to a pentose sugar group at the one position of the pyrimidinone ring. Examples of such compounds and their effects are discussed in "Molecular Basis for Serendipitous Development of Antiviral and Anticancer Aminonucleosides" by W. H. Prusoff et al; "Comparative Study of the Potency and Selectivity of Anti-Herpes Compounds" by DeClercq and "Strategy for the Development of Selective Anti-Herpes Virus Agents Based on the Unique Properties of Viral Induced Enzymes—Thymidine Kinase, DNase and DNA Polymerase". All of these articles appear in Volume 57 of a Symposium of the Federation of European Biochemical Societies, Antimetabolites in Biochemistry, Biology and Medicine edited by Skoda et al, published by Pergamon Press (1978).

Unfortunately, such antiviral compounds, based upon naturally occurring pyrimidinones have a serious disadvantage in that these compounds are rapidly metabolized, generally having a metabolic half life of less than 30 minutes. Such short metabolic life has not permitted such compounds to be effectively used under In Vivo conditions.

Certain compounds, based upon 4-Deoxo uracil have recently been synthesized by two of the inventors herein and presented in a thesis by Alan Curtis Schroeder in 1978. Such thesis does not in general discuss or suggest any anti-viral activity by 5 substituted 4-Deoxo uracil compounds except on page 98 of the thesis wherein it was indicated that such compounds would be tested against Herpes Virus in mouse L cells. There was no indication that such compounds would in fact have any effect after such tests.

BRIEF DESCRIPTION OF THE INVENTION

In accordance with the invention, there is provided a method for inhibiting the replication of the DNA virus which induces formation of thymidine kinase enzyme. In accordance with the method, the virus is exposed to an effective concentration of the compound of the formula:

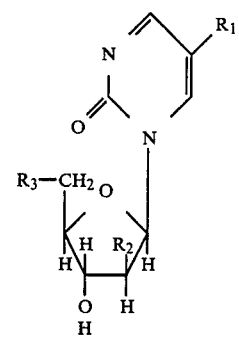

wherein $R_1$ is a radical selected from the group consisting of halogen, —$SCH_3$, —OH, alkoxy, cyano, methylamino, carboxy, formyl, nitro and unsubstituted or halosubstituted hydrocarbon groups of 1 through 3 carbon atoms; $R_2$ is hydrogen; halogen or hydroxy; and $R_3$ is hydroxy, —$OP(O)(OH)_2$, amino, or —$OCOR_4$ where $R_4$ is lower alkyl of 1 through 6 carbon atoms.

In furtherance of the invention, anti-viral compounds are provided which include those where $R_1$ of the above formula is a radical selected from the group of chloro, iodo, hydroxy, alkoxyalkyl, hydroxyalkyl, methylamino, formyl, nitro, unsubstituted hydrocarbon groups of 2 to about 3 carbon atoms or halosubstituted hydrocarbon groups of 1 to about 3 carbon atoms; $R_2$ is hydrogen or hydroxy, and $R_3$ is hydroxy, —$OP(O)(OH)_2$, amino or —$OCOR_4$ where $R_4$ is alkyl, alkenyl or alkoxyalkyl of 2 to about 18 carbon atoms.

DETAILED DESCRIPTION OF THE INVENTION

As previously discussed, the method of the invention comprises inhibiting the replication of a DNA virus which induces formation of thymidine kinase enzyme, by exposing the virus to an effective concentration of a compound of the formula:

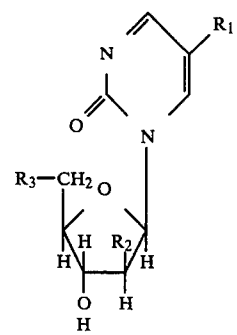

In accordance with the methods of the invention, $R_1$ of the formula is a radical selected from the group consisting of halogen, —$SCH_3$, —OH, alkoxy, cyano, methylamino, carboxy, formyl, nitro and unsubstituted or halosubstituted hydrocarbon groups of 1 through 3 carbon atoms. The most preferred $R_1$ groups are halogen, alkyl, haloalkyl, alkenyl, haloalkenyl, alkynyl or haloalkynyl groups. Particular compounds which will have good effectiveness are those compounds wherein $R_1$ is selected from methyl, ethynyl, ethyl, propyl, propynyl, iodo and bromo groups. Such compounds have been unexpectedly found to have superior effectiveness over those compounds wherein $R_1$ is $SCH_3$, —OH or alkoxy. Two particularly effective compounds having unexpected effectiveness over compounds containing an $R_1$ group which is —$SCH_3$, are those compounds wherein $R_1$ is an iodo or ethynyl group.

As previously discussed, $R_2$ is hydrogen; halogen or hydroxy but is preferably hydrogen, fluorine or hydroxy. $R_3$, as previously discussed is hydroxy, —OP(O)(OH)$_2$, amino or —OCOR$_4$ where $R_4$ is lower alkyl of 1 through 6 carbon atoms. Preferably, $R_3$ is hydroxy. Compounds wherein $R_3$ is —OP(O)(OH)$_2$, amino or —OCOR$_4$, as previously discussed, are generally in themselves, not effective but in In Vivo environments are rapidly converted to compounds wherein $R_3$ is hydroxy which then undergo further metabolic activation.

As indicated above in connection with the compounds of the present invention, $R_1$ includes various radicals like alkoxyalkyl and hydroxyalkyl. Specific representative examples include, but are not limited to, methoxymethyl, methoxyethyl, hydroxymethyl, and 2-hydroxypropyl. In addition to these radicals the compounds as disclosed hereinabove include unsubstituted hydrocarbon groups of 2 to about 3 carbon atoms or halosubstituted hydrocarbons having from 1 to about 3 carbon atoms. Typical preferred examples of such groups include ethyl, propyl, ethynyl, propynyl, and bromo-vinyl, to name but a few.

Besides hydroxy and —OP(O)(OH)$_2$ groups for $R_3$, the compounds of the present invention include esters designated by OCOR$_4$. $R_4$ may be an alkyl, alkenyl or an alkoxyalkyl radical having from 2 to about 18 carbon atoms, and include, for example, preferred members like butyl, undecyl and heptadecenyl and their isomers, such as iso-butyl, sec.-butyl, and t-butyl.

Examples of compounds suitable for use in accordance with the invention are:

1. 1-(2-Deoxy-beta-D-ribofuranosyl)-5-(methylmercapto)-2-pyrimidinone
2. 1-(2-Deoxy-beta-D-ribofuranosyl)-5-(methyl)-2-pyrimidinone
3. 1-(2-Deoxy-beta-D-ribofuranosyl)-5-(iodo)-2-pyrimidinone
4. 1-(2-Deoxy-beta-D-ribofuranosyl)-5-(bromo)-2-pyrimidinone
5. 1-(2-Deoxy-beta-D-ribofuranosyl)-5-(trifluoromethyl)-2-pyrimidinone
6. 1-(2-Deoxy-beta-D-ribofuranosyl)-5-(nitro)-2-pyrimidinone
7. 1-(2-Deoxy-beta-D-ribofuranosyl)-5-(cyano)-2-pyrimidinone
8. 1-(2-Deoxy-beta-D-ribofuranosyl)-5-(ethynyl)-2-pyrimidinone
9. 1-(2-Deoxy-beta-D-ribofuranosyl)-5-(propynyl)-2-pyrimidinone
10. 1-(2-Deoxy-beta-D-ribofuranosyl)-5-(propyl)-2-pyrimidinone
11. 1-(2-Deoxy-beta-D-ribofuranosyl)-5-(bromo-vinyl)-2-pyrimidinone
12. 1-(2-Deoxy-beta-D-ribofuranosyl)-5-(formyl)-2-pyrimidinone
13. 1-(2-Deoxy, 2-fluoro-beta-D-arabinofuranosyl)-5-(methyl)-2-pyrimidinone
14. 1-(beta-D-arabinofuranosyl)-5-(methyl)-2-pyrimidinone Two especially effective compounds for use in accordance with the present invention is the compound wherein $R_1$ is iodo or ethynyl; $R_2$ is hydrogen and $R_3$ is hydroxy.

In general, such compounds are prepared by reacting a compound of the formula:

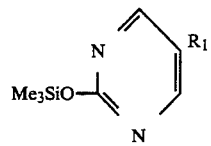

I with a substituted sugar of the formula:

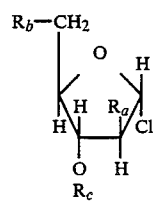

II wherein $R_a$, $R_b$ and $R_c$ are radicals which are non-reactive during the reaction of I with II and which can be converted to the desired $R_2$, $R_3$ and H respectively after reaction of I with II. Detailed discussions of how compounds for use in accordance with the method of the present invention can be prepared are found in Synthesis and Antiviral Activity of 1-(2-Deoxy-beta-D-ribofuranosyl)-5-(methylmercapto)-2-pyrimidinone by Schroeder et al published in the Journal of Medicinal Chemistry, Volume 24, No. 1, pages 109–112, available to the public Jan. 5, 1981. Further discussion of methods of synthesis of compounds for use in accordance with the method of the present invention is made by Wightman et al, Collection of Czechoslavakian Chemical Communications, Volume 38, beginning at page 1381 (1973) and "Synthesis of New Nucleoside Analogs Derived from 4-oxo Uracil and 6-substituted Uracils" by Schroeder dissertation at the State University of New York at Buffalo (1978).

In accordance with the method of the invention, the replication of numerous viruses can be inhibited. In particular, viruses which induce the formation of thymidine kinase enzyme are inhibited in accordance with the method of the invention. Such viruses generally include essentially all Herpes type viruses including Herpes simplex 1, Herpes simplex 2, varicella coster, Epstein-bar virus, Cytomegalo virus, varicella zoster, Herpes zoster and variolla. It is known that such viruses cause numerous infections in man including localized infections such as infections of the eye and genitals.

The following examples serve to illustrate and not limit the present invention.

EXAMPLE 1

1-(2-Deoxy-Beta-D-Ribofuranosyl)-5-Ethynyl-2-Pyrimidinone

A suspension of 15.06 g (67.83 mmol) of 5-iodo-2(1H)-pyrimidinone was refluxed in 40 ml of hexamethyldisilazane and 2 ml of chlorotrimethylsilane for 1 hour. The excess reagent was removed in vacuo to yield a yellow oil 5-iodo-2-trimethylsilyloxypyrimidine, which was dissolved with 30 ml of dry degassed triethylamine. To this solution was added 11.5 ml (81.37 mmol) of trimethylsilylacetylene, 0.32 g (2.5 mol%) of CuI and 0.48 g (1 mol %) of $(O_3P)_2PdCl_2$. The reaction mixture was stirred under nitrogen, at room temperature, for 3 days and diluted with 100 ml of dry THF. The mixture was filtered under dry nitrogen; the precipitate washed several times with dry THF and the filtrate was concentrated to a residue. The latter was treated with methanol to give a white crystalline, chromatographically homogeneous material 5-(2-Trimethylsilyl)ethynyl-2(1H)-pyrimidinone (9.99 g, 76.6%). Analytically pure material could be obtained by recrystallization from methanol; mp 203°–206° C.

1.41 g (7.32 mmol) of 5-(2-trimethylsilylethynyl)-2(1H)-pyrimidinone was refluxed in 14 ml of hexamethyldisilazane and 0.3 ml of chlorotrimethylsilane for 3 hours, and the resulting solution was concentrated to an oily residue. The residual solvent was removed by co-evaporation with 1,2-dichloroethane (2×20 ml). The residue was dissolved in 30 ml of anhydrous dichloroethane and the solution was added to a cooled solution of 2.5 g (5.82 mmol) of the halogenose 1-(3,5-di-O-(p-chlorobenzoyl)-2-deoxy-alpha-D-ribofuranosyl)chloride. The cooled mixture was then treated, dropwise, with a solution of 0.17 ml of $SnCl_4$ in 25 ml of anhydrous 1,2-dichloroethane. The mixture was stirred at 0° C. for 2 hours and periodically monitored by tlc (15% ethyl acetate in methylene chloride; Macherey-Nagel silica gel G). The mixture was diluted with dichloroethane (100 ml) and saturated bicarbonate solution (50 ml), and filtered over Celite, the residue being washed several times with dichloroethane. The organic layer was subsequently washed with water (50 ml), dried over $MgSO_4$, and concentrated to a residue which was chromatographed on 100 g of silica gel (eluted with a gradient of 0 to 12% ethyl acetate in methylene chloride). The fractions containing the slower moving alpha anomer, 1-(3,5-di-O-(p-chlorobenzoyl)-2-deoxy-alpha-D-ribofuranosyl)-5-(2-trimethylsilyl)-ethynyl-2-pyrimidinone, were pooled, concentrated to a white residue which was recrystallized from ethanol to provide, after drying, 0.48 g (14.2%); mp 150°–152° C.

The faster moving beta anomer, 1-(3,5-di-O-(p-chlorobenzoyl)-2-deoxy-beta-D-ribofuranosyl)-5-(2-trimethylsilyl)ethynyl-2-pyrimidinone, was obtained in a similar manner to that described for the alpha anomer. After recrystallization from ethanol and drying, 0.42 g (12.4%) of the white powder was obtained; mp 183°–185° C.

0.31 g (0.5 mmol) of the beta anomer was then added to 20 ml of cold anhydrous methanol presaturated with dry ammonia, and the mixture, after sealing the reaction vessel, was stirred at 4° C. for 6 hours. The resulting solution was concentrated to an oil; the latter was treated with acetone and concentrated to a minimum volume with concomitant precipitation of the product. The mixture was treated with small amounts of acetone-ether and cooled. The product, 1-(2-deoxy-beta-D-ribofuranosyl)-5-ethynyl-2-pyrimidinone, was collected by filtration, washed with acetone-ether and dried to yield 69 mg (55.9%) of the off-white powder; dec above 130° C.;

NMR (DMSO-$d_6$+$D_2O$) delta 2.26 (m, 2, 2'-H), 3.68 (m, 2, 5'-H), 3.97 (m, 1, 4'-H), 4.27 (m, 2, 3'-H and C≡C—H), 6.03 (t, 1, 1'-H); $J_{1',2'}=6$ Hz), 8.63 (d, 1, 6-H, $J_{6,4}=3$ Hz), 8.73 (d, 1, 4-H, $J_{4,6}=3$ Hz);

IR (KBr) Nu max 3525 (shoulder), 3220 (broad), 2925 (shoulder), 2100, 1660, 1423, 1350, 1265, 1110, 1070 (shoulder), 925 cm$^{-1}$;

UV (MeOH) lambda max 332 nm Anal. ($C_{11}H_{12}N_2O_4$); C, H, N.

EXAMPLE 2

1-(2-Deoxy-Beta-D-Ribofuranosyl)-5-(1-propynyl)-2-pyrimidinone 31.67 g (0.13 mol) of 5-iodo-2-methoxypyrimidine, 0.73 g (2.9 mol %) of CuI and 1.02 g (1.1 mol%) of bis(triphenylphosphine)$PdCl_2$ were suspended in 200 ml of anhydrous triethylamine (distilled over BaO) in a Parr pressure bottle. The bottle was evacuated and filled with 85% propyne. The bottle was repeatedly shaken and filled with propyne until the pressure had stabilized at 20 psi, and then the mixture was shaken, in a Parr hydrogenator, for 24 hours. More propyne was added at this time and shaking was continued for an additional 48 hours. On tlc (methylene chloride), there was only one major product; no starting material was observed. The mixture was diluted with methylene chloride (300 ml), washed with saturated bicarbonate solution (2×60 ml), dried over magnesium sulfate and concentrated to a minimum volume with attendant precipitation. Petroleum ether was added to the mixture and after cooling, the first crop was obtained by filtration. The filtrate was concentrated to give a second crop. Both crops were dried and sublimed at 0.3 mm Hg (max. oil bath temp. 100° C.) to yield (15.26 g (76.7%) of analytically pure, white-crystalline material, 2-methoxy-5-(1-propynyl)pyrimidine; mp 88°–89.5° C.).

Chlorotrimethylsilane (4.11 ml; 32.5 mmol) was introduced by syringe, into a solution of 1.5 g (10.2 mmol) of the 2-methoxy-5-(1-propynyl)pyrimidine and 4.56 g (30.44 mmol) of NaI in 35 ml of anhydrous acetonitrile maintained under an atmosphere of dry nitrogen and removed from light. The mixture was stirred at 50° C. for 2-½ hours with periodic monitoring by tlc. The mixture was cooled in an ice-bath and 3.5 g (8.14 mmol) of the halogenose, 1-(3,5-di-O-(p-chlorobenzoyl)-2-deoxy-alpha-D-ribofuranosyl)-chloride were then added. To this mixture was added 3 ml of 1N trimethylsilyl triflate in 1,2-dichloroethane; the mixture was stirred at 0° C. for 1 hour and then at room temperature for 2-½ hours. The reaction mixture was then diluted with dichloromethane (150 ml) and saturated aqueous bicarbonate (65 ml). The organic extract was subsequently washed with water (60 ml), dried over magnesium sulfate and concentrated to a residue which was subjected to flash chromatography on 80 g of silica gel. The fractions containing the slower moving alpha anomer were pooled and concentrated to a minimum volume with attendant precipitation. The mixture was cooled and filtered; the white product washed with diethyl ether and dried at 50° C. to provide 1.1 g (25.7%) of 1-(3,5-di-O-(p-chlorobenzoyl)-2-deoxy-alpha-D-ribofuranosyl)-5-(1-propynyl)-2-pyrimidinone; mp 176°–178° C.

The fractions containing the faster moving beta anomer 1-(3,5-di-O-(p-chlorobenzoyl)-2-deoxy-beta-D-ribofuranosyl)-5-(1-propynyl)-2-pyrimidinone were pooled and concentrated to yield a foam which was subsequently dried.

300 mg (0.57 mmol) of the beta anomer was added to a cold, anhydrous, saturated solution of methanolic ammonia (15 ml), and the flask was sealed. The mixture was stirred at 4° C. for 4 hours. Tlc (10% MeOH/CH$_2$Cl$_2$) showed several minor fluorescent products. The solution was concentrated, in vacuo, to an oil which was chromatographed on 20×20 cm silica gel plates (10% MeOH/CH$_2$Cl$_2$). The major fluorescent band was extracted with a solution of 20% methanol in methylene chloride and the extract was concentrated to a syrup. The latter was dried to give 1-(2-deoxy-beta-D-ribofuranosyl)-5-(1-propynyl)-2-pyrimidinone as a pale yellow, chromatographically homogeneous foam (82 mg; 57.7%);

NMR (DMSO-d$_6$+D$_2$O) delta 1.18 (t, ethanol, H$_2$O), 1.83–2.67 (m, 5, H'-2 and —C≡CH$_3$), 3.53–4.5 (ethanol, H$_2$O and sugar protons), 6.08 (t, 1, H'-1, J$_{1',2'}$=6 Hz), 7.97 (dd, 2. H-4 and H-6; J$_{4,6}$=3 Hz);

IR (KBr) Nu max 3350 (broad), 2920 (shoulder), 2600 (shoulder), 1650, 1500, 1250, 1090 cm$^{-1}$;

Anal. (C$_{12}$H$_{14}$N$_2$O$_4$.0.4H$_2$O) C, H, N.

EXAMPLE 3

1-(2-Deoxy-beta-D-Ribofuranosyl)-5-iodo-2-pyrimidinone

2-Pyrimidinone (6 g, 62.44 mmol) and N-iodosuccinimide (14.7 g, 65.3 mmol) in dry DMF (30 ml) were stirred for 48 hours at room temperature with the exclusion of both light and moisture. The mixture was added to ether (50 ml) with stirring and the supernatant was decanted. The precipitate was collected by filtration, repeatedly washed with acetone and finally with methanol, until the filtrate became light yellow. After drying in vacuo the yellow granular product, 5-iodo-2(1H)-pyrimidinone, appeared to be pure by tlc and spectra, but the elemental analysis indicated that it was contaminated with a trace amount of DMF. Yield: 11.35 g (77.5%).

A suspension of 0.86 g (3.87 mmol) of the 5-iodo-2(1H)-pyrimidinone in 15 ml of hexamethyldisilazane and 0.3 ml of chlorotrimethylsilane was refluxed for 2 hours (with the exclusion of moisture), cooled and concentrated in vacuo to yield a yellow oil. Residual solvent was removed by coevaporation with 1,2-dichloroethane (2×10 ml). 1.65 g (3.84 mmol) of the sugar halide 1-(3,5-di-O-(p-chlorobenzoyl)-2-(deoxy-alpha-D-ribofuranosyl) chloride, were added to the oil; the mixture was dissolved in 50 ml of anhydrous 1,2-dichloroethane and cooled in an ice bath. To the cooled solution was added, dropwise, a solution of 0.2 ml (1.7 mmol) of SnCl$_4$ in 25 ml of anhydrous dichloroethane. The reaction mixture was stirred at 0° C. for 2-½ hours at which time tlc (17% ethyl acetate in dichloroethane) showed disappearance of the starting material, indicating that the reaction was essentially complete. The mixture was diluted with 60 ml of dichloroethane and 50 ml of saturated bicarbonate, and the resulting emulsion was filtered over Celite, the precipitate being washed several times with 1,2-dichloroethane. The organic layer was washed with 50 ml of water, dried over anhydrous magnesium sulfate and concentrated to a residue which on tlc showed two major spots of equal intensity (R$_f$ values 0.19 for the alpha anomer, 1-[3,5-di-O-(p-chlorobenzoyl)-2-deoxy-alpha-D-ribofuranosyl]-5-iodo-2-pyrimidinone, and 0.3 for the beta anomer 1-[3,5-di-O-(p-chlorobenzoyl)-2-deoxy-beta-D-ribofuranosyl]-5-iodo-2-pyrimidinone; 17% ethyl acetate dichloroethane; Macherey-Nagel silica gel G). This residue was chromatographed on 90 g of silica gel and eluted with a gradient of 0 to 25% ethyl acetate in dichloroethane. The fractions, containing the slower moving alpha anomer were pooled, concentrated to a residue which weighed, after drying, 0.48 g (20.14%). The white crystalline compound was obtained by recrystallization from ethanol-acetone; mp 175°–176° C.; [alpha]$_D^{26}$= +20.03° (CHCl$_3$, c.0.108);

NMR (CDCl$_3$) delta 2.88 (m, 2, 2'-H), 4.6 (d, 2, 5'-H), 5.0 (t, 1, 4'-H), 5.65 (d, 1, 3'-H), 6.27 (d, 1, 1'-H, J$_{1',2'}$=7 Hz), 7.25–8.12 (m, 8, phenyl), 8.18 (d, 1, 6-H, J$_{6,4}$=3 Hz), 8.68 (d, 1, 4-H, J$_{4,6}$=3 Hz);

IR (CHCl$_3$ Nu max 3000, 1725, 1665, 1595, 1490, 1380, 1260, 1090, 1010 cm$^{-1}$;

UV (CHCl$_3$) lambda max (epsilon max) 340 nm (3600).

Anal. (C$_{23}$H$_{17}$Cl$_2$IN$_2$O$_6$) C, H, Cl, I, N.

The faster moving beta anomer was obtained in the same manner descrbed for the alpha anomer to yield 0.46 g (19.5%) of 1-(3,5-di-O-(p-chlorobenzoyl)-2-deoxy-beta-D-ribofuranosyl)-5-iodo-2-pyrimidinone; mp 136°–138° C.; [alpha]$_D^{26}$= −13.66° (CHCl$_3$, c 0.10);

'H NMR (CDCl$_3$) delta 2.32 (m, 1, 2'-H) 3.2 (m, 1, 2'-H), 4.75 (m, 3, 4'-H, and 5'-H), 5.62 (d, 1, 3'-H), 6.27 (t, 1, 1'-H, J$_{1',2'}$=7 Hz), 7.30–8.17 (m, 8, aromatic), 8.27 (d, 1, 6-H, J$_{6,4}$=3 Hz), 8.57 (d, 1, 4-H, J$_{4,6}$=3 Hz);

IR (CHCl$_3$) Nu max 3000, 1725, 1675, 1595, 1500, 1380, 1260, 1090, 1010 cm$^{-1}$;

UV (CHCl$_3$) lambda max (epsilon max) 341 nm (3500).

Anal. (C$_{23}$H$_{17}$Cl$_2$IN$_2$O$_6$) C, H, Cl, I, N.

0.41 g (0.67 mmol) of the beta anomer was added to a cold anhydrous solution of methanolic ammonia (25 ml); the flask was sealed and the mixture was stirred at 4° C. for 5 hours. The reaction was complete as indicated by tlc (10% MeOH/CH$_2$Cl$_2$). The solution was concentrated to a syrup which was subsequently treated with acetone and chilled (−20° C.) to give, after several days, the crystalline material 1-(2-deoxy-beta-D-ribofuranosyl)-5-iodo-2-pyrimidinone. The product was collected by filtration, washed with acetone and dried, to provide 100 mg (45.1%) of the pale yellow material, 160°–170° C. (decomposes).

'H NMR (DMSO-d$_6$) delta 2.35 (m, 2, 2'-H), 3.65 (m, 2, 5'-H), 3.90 (m, 1, 4'-H), 4.22 (m, 1, 3'-H), 5.22 (t, 2, OH), 6.0 (t, 1, 1'-H); J$_{1',2'}$=6 Hz), 8.62 (d, 1, 6-H, J$_{6,4}$=3 Hz), 8.75 (d, 1, 4-H).

IR (KBr) Nu max 3390, 3140, (broad), 2925, 1640, 1600 (shoulder), 1500, 1390, 1290, 1250, 1100, 1070 cm$^{-1}$;

UV (MeOH) lambda max (epsilon max) 335 nm (2830).

Anal. (C$_9$H$_{11}$IN$_2$O$_4$) C, H, I, N.

EXAMPLE 4

The substituted pyrimidinone of Example 3, 1-(2-deoxy)-beta-D-ribofuranosyl)-5-iodo-2-pyrimidinone (IPdR) was tested in vivo. Three groups of five Swiss Webster Balb/C mice weighing from 19 to 23 grams were implanted with HSV-2 (333 strain) with a virus load of 5×10$^5$ plaque forming units.

Drug administration began one day following virus implant. The IPdR was administered subcutaneously to a first group of mice and intraperitoneally to a second group of mice. The third group of mice which performed as controls were not given any IPdR. The dosage of IPdR was at the rate of 100 mg/kg twice daily for 2.5 days for a total of 5 doses. The results are provided in Table 1 below:

TABLE 1

| GROUP | DAYS-SURVIVAL |
|---|---|
| Control | 5 out of 5 died (9.4 days average) |
| Subcutaneous IPdR | 1 died on day 11; 2 died on day 13 (12 days average) 2 long term survivors* |
| Intraperitoneal IPdR | 1 died on day 17 4 long term survivors* |

*>30 days

EXAMPLE 5

In accordance with the present invention, 1-(2-Deoxy-beta-D-ribofuranosyl)-5-(methylmercapto)-2-pyrimidinone is prepared essentially in accordance with the procedure set forth in "Synthesis and Antiviral Activity of 1-(2-Deoxy-beta-D-ribofuranosyl)-5-(methylmercapto)-2-pyrimidinone" by Schroeder and Bardos and Cheng, Volume 24, page 109, January 1981. HeLa cells were infected in 1640 RPMI medium with herpes simplex type 1 (HSV-1) and independently with herpes simplex type 2 (HSV-2) virus at a multiplicity of 5 to 10 plague forming units per cell. The composition of 1640 RPMI medium is reported in "Biological Activity of 5 Ethyl, 5 Propyl, and 5 Vinyl 2'-Deoxyuridine" by Cheng et al published in Antimicrobial Agents Chemotherapy, Volume 10, beginning at page 19 (1976). 1640 RPMI medium is commercially available from Gibco Company, Grand Island, N.Y. After 1 hour, virus absorption, the drugs were added. Resulting cultures were analyzed for virus titer at 24 hours post infection a described in the procedure set forth in "Biological Activity of 5-Ethyl, 5-Propyl and 5-Vinyl 2'-Deoxy uridine" by Cheng et al. The results are set forth in Table 2. The numbers set forth in Table 2 show the number of plaque forming units in the control which contained no methylmercapto compound and the number of units at concentrations of 100, 200 and 400 micromoles of the methylmercapto compound. The results clearly indicate substantial decrease in the number of plaque forming units in the presence of 1-(2-Deoxy-beta-D-ribofuranosyl)-5-(methylmercapto)-2-pyrimidinone.

TABLE 2

| compound conc., M | plaque-forming units/mL | |
|---|---|---|
|  | HSV-1(Kos) | HSV-2 (333) |
| 0 | $1.5 \times 10^7$ | $1.2 \times 10^7$ |
| 100 | $6.4 \times 10^6$ | $1.3 \times 10^7$ |
| 200 | $1.7 \times 10^6$ | $3.1 \times 10^6$ |
| 400 | $3.4 \times 10^5$ | $3.2 \times 10^5$ |

EXAMPLE 6

The methylmercapto composition, as described in Example 5. was tested for binding affinity with thymidine kinase from various sources. Viruses which induce the production of thymidine kinase, induce thymidine kinase specific to the virus. Tests of the binding affinity of the methylmercapto compound with thymidine kinase extracted from human cells showed little binding affinity; whereas, the binding affinity of the methylmercapto compound with thymidine kinase extracted from cells infected with herpes simplex 1 virus and with Varicella zoster virus infected cells, showed great binding affinity. It is believed that the compound of the invention, in order to become active in inhibiting the replication of the virus, must become phosphorylated. For such phosphorylation to occur, the thymidine kinase must first bind to the compound. Since binding with thymidine kinase produced by the virus is much more efficient and effective than binding with thymidine kinase from other sources, phosphorylation of the compound occurs more rapidly in the presence of active viruses producing thymidine kinase. The compound, activated by phosphorylation, then is able to interfere with replication of the virus.

EXAMPLE 7

1-(2-Deoxy-beta-D-ribofuranosyl)-5-(methyl)-2-pyrimidinone, also known as 4-Deoxothymidine, was prepared by thionation of the 4-oxo group of diacetylated thymidine with phosphorus pentasulfide, followed by desulfuration of the 4-thiothymidine derivative by Raney nickel reduction. The method for preparation of the above described methyl compound is essentially the same as described by Wightman et al in Collection of Czechoslavakian Chemical Communications, Volume 38, beginning at page 1381 (1973).

The above described methyl compound was tested for viral inhibition substantially in accordance with the method of Example 5 except that the concentration were 50 and 100 micromolar. The methyl compound showed a 95.5% inhibition for HSV-1 at 50 micromoles when compared with an untreated control and an 87.9% inhibition for HSV-2 when compared with an untreated control. By comparison, methylmercapto compounds of Example 5 at the same 50 micromolar concentration showed only a 41.4% inhibition for HSV-1 virus and a 57.2% inhibition for HSV-2 virus. At 100 micromolar concentration, a 99% inhibition was shown for the methyl compound for HSV-1 virus and a 98.3% inhibition was shown for HSV-2 virus. Again, by comparison, the methylmercapto compound of Example 5 only showed a 83.8% inhibition for HSV-1 and a 79.3% inhibition for HSV-2. The dramatically superior inhibition for the methyl compound is unexpected.

What is claimed is:

1. A compound which is 1-(2-Deoxy-beta-D-ribofuranosyl)-5-(ethynyl)-2-pyrimidinone.

2. A compound which is 1-(2-Deoxy-beta-D-ribofuranosyl)-5-(propynyl)-2-pyrimidinone.

3. A compound which is 1-(2-Deoxy-beta-D-ribofuranosyl)-5-(bromo-vinyl)-2-pyrimidinone.

* * * * *

UNITED STATES PATENT AND TRADEMARK OFFICE
CERTIFICATE OF CORRECTION

PATENT NO. : 4,782,142

DATED : Nov. 1, 1988

INVENTOR(S) : Thomas J. Bardos et al.

It is certified that error appears in the above-identified patent and that said Letters Patent is hereby corrected as shown below:

In column 1, line 14, insert --This invention was developed under National Cancer Institute Grant 5-ROI-CA-06695. The United States Government has certain rights in this invention.--

Signed and Sealed this

Twenty-first Day of September, 1993

Attest:

BRUCE LEHMAN

Attesting Officer

Commissioner of Patents and Trademarks